United States Patent [19]

Lang et al.

[11] Patent Number: 4,994,263
[45] Date of Patent: Feb. 19, 1991

[54] MEDICINAL COMBINATION USED IN PHOTOCHEMOTHERAPY

[75] Inventors: Gerard Lang, Saint Gratien; Andre Deflandre, Orray la Ville; Irena Beck, Villepinte, all of France

[73] Assignee: L'Oreal, Paris, France

[21] Appl. No.: 517,520

[22] Filed: Apr. 30, 1990

Related U.S. Application Data

[63] Continuation of Ser. No. 625,391, Jun. 28, 1984, abandoned.

[30] Foreign Application Priority Data

Jun. 27, 1984 [LU] Luxembourg ............................ 85438

[51] Int. Cl.$^5$ .......................... A61K 7/40; A61K 7/42; A61K 7/44
[52] U.S. Cl. .......................................... 424/59; 424/47; 424/60; 514/861; 514/863; 514/864; 514/886; 514/887; 514/937; 514/938; 514/939; 514/944; 514/945; 514/960; 514/969
[58] Field of Search ..................................... 424/59, 60

[56] References Cited

U.S. PATENT DOCUMENTS

| | | | |
|---|---|---|---|
| 3,448,190 | 6/1969 | Baron et al. ............. | 424/59 |
| 4,284,621 | 8/1981 | Preuss et al. ............. | 424/59 |
| 4,290,974 | 9/1981 | Bouillon et al. ........... | 260/511 |
| 4,406,880 | 9/1983 | Bouillon et al. ........... | 424/40 |
| 4,464,354 | 8/1984 | Bisagni ................... | 424/59 |

FOREIGN PATENT DOCUMENTS

| | | | |
|---|---|---|---|
| 3115033 | 1/1983 | Fed. Rep. of Germany ........ | 424/59 |
| 2236515 | 2/1975 | France ................... | 424/59 |
| 2282426 | 3/1976 | France ................... | 424/59 |
| 2383904 | 10/1978 | France ................... | 424/59 |
| 2430938 | 2/1980 | France ................... | 424/59 |
| 0022642 | 2/1980 | Japan .................... | 424/59 |

OTHER PUBLICATIONS

Archives of Dermatology, 7/76, vol. 112, pp. 943-950, Wolff.
Photochemotherapie Der Psoriasis, 7/76, pp. 1 to 9, Hoffman.
Intermistische Information Brochure, 10/75, pp. 2 to 4.
Journal of Investigative Dermatology, 1959, vol. 32, pp. 255-262, Pathak.
Journal of Investigative Dermatology, 1958, vol. 31, pp. 289-295, Griffin.
Fitzpatrick, Journ. of Investigative Dermatology, 1950, vol. 32, p. 349.
Elliot, Journ. of Investigative Dermatology, 1959, vol. 32, pp. 339 & 340.
Kanof, Journ. of Investigative Dermatology, 1959, vol. 32, pp. 343 & 344.
Photochemotherapie Der Psoriasis, 7/1976, pp. 1 to 91, Hoffman.
Arnold, Journ. of Invest. Dermatology, 1959, vol. 32, pp. 341 and 342.
Imbrie et al., Journ. of Invest. Dermatology, 19, vol. 32, pp. 331 to 337.
Daniels et al., Journ. of Invest. Dermat., 19, vol. 32, pp. 321 to 329.
London, Journ. of Invest. Dermat., 1959, vol. 32, pp. 315-317.
Pathak, Journ. of Invest. Dermat., 1959 vol. 32 pp. 255-262.
Becker, Journ. of Invest. Dermat., 1959, vol. 32, pp. 263-267.
Zimmerman, Journ. of Invest. Dermat., 19, vol. 32 pp. 269-271.
Cosmetics & Toiletries, 3/1976, vol. 91, p. 93.
Stegmaier, Journ. of Invest. Dermat., 19, vol. 32, pp. 345-349.
Fowlks, Journ. of Invest. Dermat., 19, vol. 32, pp. 249-254.

Primary Examiner—Dale R. Ore
Attorney, Agent, or Firm—Fleit, Jacobson, Cohn, Price, Holman & Stern

[57] ABSTRACT

A composition for treatment and treatment of certain skin diseases is disclosed. The treatment combines furocoumarins, UV-A radiation, and a benzylidenecamphor derivative. The composition and treatment produces the desirable results of the furocoumarin/UV-A radiation treatment without the undesirable phototoxic side effects.

11 Claims, No Drawings

MEDICINAL COMBINATION USED IN PHOTOCHEMOTHERAPY

This application is a continuation of application Ser. No. 625,391, filed June 28, 1984, abandoned.

Photochemotherapy has been developed recently, especially with a view to the treatment of certain skin diseases such as the different varieties of psoriasis, chronic dermatoses, such as palmar and plantar dermatoses, herpes simplex, vitiligo and alopecia areata. This treatment is based on the interaction of ultraviolet light, situated in the UV-A range, combined with administration of photoactive derivatives chosen from the family of the furocoumarins.

This treatment is more especially referred to as "PUVA therapy", which stands for psoralene plus UVA.

Since the penetration of UV-A rays is limited to the surface layers of the skin and the photoactivation of psoralene only occurs at these wavelengths, the said therapeutic treatment has made it possible to confine a skin chemotherapy to the surface, thus protecting other tissues from possible cytotoxic effects.

The use of the furocoumarins, whether they are of natural or synthetic origin, in PUVA therapy however suffers from a certain number of disadvantages because of certain skin disorders which reveal themselves in violent erythemas, eczematiform lesions followed by irregular residual pigmentation, especially in the case of topical application of furocoumarins.

These skin reactions following exposure to ultraviolet light are referred to as "phototoxic reactions", which produce accelerated ageing of healthy skin.

The same is true in the case of oral administration of furocoumarin derivatives followed by exposure to intense ultraviolet radiation in an irradiation cabin at the instant at which the furocoumarin concentration at the skin and in the blood circulation is a maximum. In general, a violent erythema results after each exposure, and accelerated ageing of the skin results after the tens of exposures which a complete treatment comprises.

In spite of the great value of this therapeutic treatment, these phototoxic reactions present a problem for the use of this therapy. Thus, during the treatment the patient is often recommended to wear spectacles which efficiently filter out ultraviolet rays, so as to avoid incipient cataract and to protect himself from the sun after ingestion of the furocoumarins so as not to exacerbate the effects of the exposure to ultraviolet in the cabin.

The Applicants has now found, surprisingly, that it was possible significantly to reduce the harmful secondary effects resulting from the use of furocoumarins in photochemotherapy on skin which is free from lesions, by the use of benzylidene-camphor or of its derivatives, without however detracting from the therapeutic effect on the lesions which it is desired to treat.

The expression "benzylidene-camphor or its derivatives" encompasses compounds which absorb radiation in the UV-A range as well as those which absorb radiation in the UV-B range.

This effect appears to be due - without this explanation imposing any limitation - to the fact that benzylidene-camphor or its derivatives are capable of deactivating the triplet level of the furocoumarins in accordance with the equation:

$$Pso^x + Bz-C \rightarrow Pso + Bz-c^x$$

Pso is psoralene and Bz - C is benzylidene-camphor or its derivatives. In effect, the action of the furocoumarins appears to be due to the fact that the latter are electronically excited upon absorption of the ultraviolet light and it is the excited triplet level which is a precursor of all the known photobiological reactions.

Because of the use of benzylidene-camphor or of its derivatives the furocoumarin molecule is returned to a non-excited base state and the excited molecule of benzylidene-camphor or of its derivatives then undergoes deactivation by an $E \rightleftarrows Z$ intramolecular isomerization in accordance with the following equation:

$$Bz-C^x \rightarrow \tfrac{1}{2}Bz-C\,(E) + \tfrac{1}{2}Bz-C(Z)$$

Experiments carried out by the Applicants have in particular shown that a concentration of benzylidene-camphor or of its derivatives of about $4.10^{-3}$ mole per liter was sufficient strongly to inhibit the photoaddition reactions of furocoumarins with AND and of photoreticulation of AND to substantial degrees, these reactions being the origin of the phototoxicity of the furocoumarins.

Other experiments, in vivo, have shown that the use of a filtering composition containing benzylidene-camphor or its derivatives, used individually or as a mixture, attenuates to a high degree the phototoxicity reactions produced in healthy skin by ingestion or topical application of furocoumarins followed by ultraviolet irradiation.

Thus, by combining, in photochemotherapy, a treatment based on furocoumarins with a treatment based on benzylidene-camphor or its derivatives, it is possible for the patients to lead a virtually normal life without having to hide from sunlight during the treatment.

The present invention thus relates to the combination, in photochemotherapy and in particular in PUVA therapy, of furocoumarins and benzylidene-camphor or its derivatives.

Other subjects of the invention will emerge on reading the description and examples which follow.

The medicinal combination according to the invention, intended to be used in photochemotherapy, is essentially characterized in that it comprises a furocoumarin and benzylidene-camphor or one of its UV-filtering derivatives, the compounds being used separately and, if appropriate, at staggered times, within the scope of the said treatment.

The ultraviolet-filtering benzylidene-camphor derivatives are more especially chosen from among: benzylidene-camphor, p-methyl-benzylidene-camphor and 3-p-oxybenzylidene-bornan-2-ones of French Patent No. 2,430,938 having the formula:

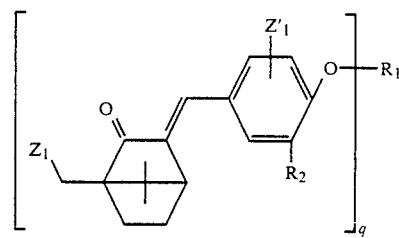

in which:

$Z_1$ and $Z'_1$ are respectively a hydrogen atom or an $SO_3H$ radical or a salt of this sulfonic acid with an inorganic or organic base, with at least one of the two radicals $Z_1$ or $Z'_1$ representing a hydrogen atom;

$R_1$ is a hydrogen atom, an optionally branched alkyl radical containing 2 to 18 carbon atoms, an alkenyl radical containing 3 to 18 carbon atoms or a

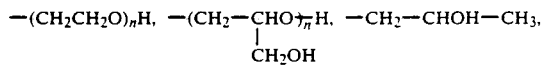

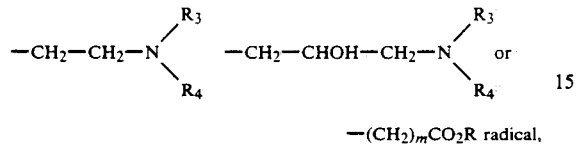

in which R is H, an alkyl radical containing 1 to 8 carbon atoms, $-(CH_2)_3-SO_3H$ or a salt of this acid with an organic or inorganic base, or a divalent radical $-(CH_2)_m$ or $-CH_2-CHOH-CH_2$, m has a value of 1 to 10, n has a value of 1 to 6 and $R_3$ and $R_4$ each represent a hydrogen atom or an optionally branched or hydroxylated alkyl radical or together form a heterocyclic aminoaliphatic radical with the nitrogen atom, $R_2$ is a hydrogen atom, an alkoxy radical containing 1 to 4 carbon atoms or a divalent radical 'O— bonded to the $R_1$ radical if the latter is also divalent, q is 1 or 2, it being understood that if q has a value of 2, $R_1$ is a divalent radical and that if $R_1$ is hydrogen, $R_2$ is also hydrogen and moreover, if $R_2$ is alkoxy, $R_1$ can also be methyl; the benzylidene-camphors described in Belgian Patent No. 897,051 and having the formula:

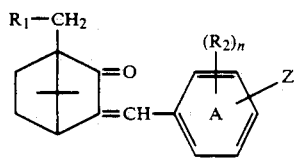

in which $R_1$ is a hydrogen atom or a $-SO_3^{\oplus}M^{\ominus}$ radical, where M is a hydrogen atom, an alkali metal or an $N^{\oplus}(R_3)_4$ group, $R_3$ being a hydrogen atom or a $C_1$-$C_4$ alkyl or hydroxyalkyl radical, $R_2$ is a $C_1$-$C_4$ alkyl radical which may be linear or branched, or a $C_1$-$C_4$-alkoxy radical, n being an integer ranging from 0 to 4 and, if $n \geq 2$, the radicals $R_2$ can be identical or different, and Z represents a

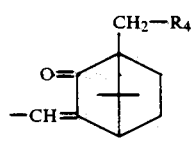

group, in which $R_4$ has the same meanings as $R_1$ and can be identical with or different from $R_1$, or Z represents a group

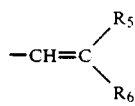

in which $R_5$ is a hydrogen atom, a $C_1$-$C_4$-alkyl radical, an aryl radical optionally substituted by halogen atoms or by $C_1$-$C_4$-alkyl or alkoxy groups, a —CN, —$COOR_7$ or

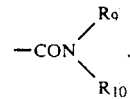

group and $R_6$ is a

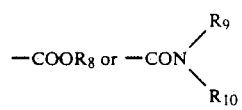

group, where $R_7$ and $R_8$, which may be identical or different, are alkyl, alkenyl, cycloalkyl or aralkyl radicals containing at most 20 carbon atoms and optionally substituted by hydroxyl, alkoxy, amine or quaternary ammonium groups and $R_9$ and $R_{10}$, which may be identical or different, are a hydrogen atom or alkyl, alkenyl, cycloalkyl or aralkyl radicals containing at most 20 carbon atoms and optionally substituted by hydroxyl, alkoxy, amine or quaternary ammonium groups, or, if $R_5$ is a hydrogen atom, or an optionally substituted aryl or alkyl radical, $R_6$ can also represent a $-COO^{\ominus}M^{\oplus}$ radical, M being defined as above, the two radicals, namely the methylidene-camphor radical on the one hand and Z on the other hand, being fixed to the aromatic ring A either in the para-position or in the meta-position relative to one another, the sulfonamides derived from the benzylidene-camphor described in Belgian Patent No. 897,241 and having the formula:

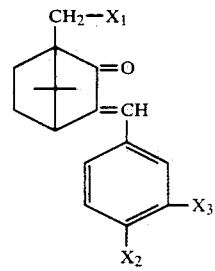

in which $X_1$ is a hydrogen atom of the radical Y, $X_2$ is a hydrogen or halogen atom, a $C_1$-$C_4$-alkyl or alkoxy radical or a radical Y or Z, $X_3$ is a hydrogen or halogen atom, a $C_1$-$C_4$-alkyl or alkoxy radical or a Y or Z radical, Y denotes the

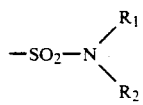

group in which $R_1$ is a hydrogen atom or a $C_1$-$C_4$-alkyl or hydroxyalkyl radical, $R_2$ is a hydrogen atom or a linear or branched alkyl or alkenyl radical or a cycloalkyl, aryl or aralkyl radical, it being possible for these various $C_1$-$C_{20}$ radicals to be substituted by one or more hydroxyl, alkoxy or dialkylamino groups, but $R_1$ and $R_2$ cannot simultaneously be a hydrogen atom, and Z is one of the following groups: $Z_1 =$

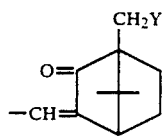

where Y has the meaning given above, or $Z_2 =$

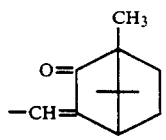

or

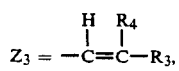

where $R_3$ is a hydrogen atom or a —CN or $COR_5$ radical, $R_4$ is a —$COR_6$ radical and $R_5$ and $R_6$, which may be identical or different, are $C_1$–$C_{20}$-alkoxy or alkyl-amino groups, with the proviso that one of the symbols $X_1$, $X_2$ and $X_3$ is different from the two others and that:

(a) if $X_1$ is a hydrogen atom, $X_2$ and $X_3$ are different from one another and cannot have the meaning of $Z_2$ and $Z_3$, one of the two obligatorily having the meaning of Y or $Z_1$, and (b) if $X_1$ has the meaning of Y, $X_2$ and $X_3$ are different from Y and cannot simultaneously have the meaning of $Z_1$ or $Z_2$ or $Z_3$;

the benzylidene-camphor derivatives containing a quaternary ammonium radical on the benzene ring in the para-position relative to the bornylidene radical, according to French Patent No. 2,199,971, and having the formula:

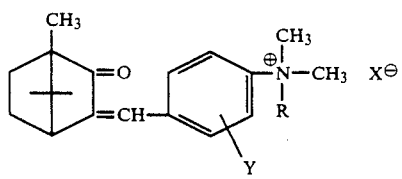

in which R represents a hydrogen atom or an alkyl group containing 1 to 12 carbon atoms, Y represents a halogen, a methyl group or a hydrogen atom and X⁻ represents a halide, an arylsulfonate, an alkylsulfonate, a camphosulfonate or an alkyl-sulfate;

the benzylidene-camphor derivatives which are sulfonated at the methyl radical in the 10-position of the camphor or in the 3'- or 4'-position of the benzene ring, according to French Patents No. 2,236,515 and 2,282,426 and which respectively have the formulae:

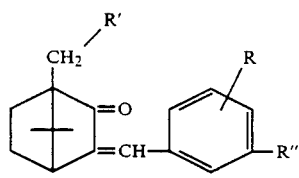

in which R is a hydrogen atom, a halogen atom, such as Cl or F, or an alkyl radical containing 1 to 4 carbon atoms and R' and R" are each a hydrogen atom, a —$SO_3M$ radical in which M is H, an organic ammonium group or a metal, at least one of the radicals R' and R" having a meaning other than H, and

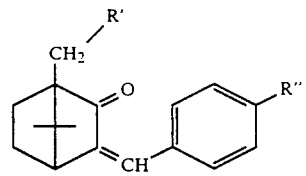

in which R' is a hydrogen atom or a —$SO_3M$ radical and R" is $SO_3M$, in which M is H, an organic ammonium group or a metal;

the p-methylbenzylidene-camphor derivatives, substituted at the p-methyl group, according to French Patents No. 2,383,904, 2,402,647 and 2,421,878, which respectively have the formulae:

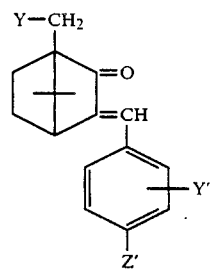

in which Y and Y' are H or $SO_3H$ and the corresponding salts with organic or inorganic bases, at least one of the radicals Y and Y' having the meaning H, Z' is the —$CH_2R$, —CHR'R', —CHO, or —COOR" groups, with R=—$OR_4$, —$OCOR_5$ —$SR_6$, —CN or —COOR", $R_4$ is H, alkyl, polyoxyethylene, substituted or unsubstituted aryl, menthyl or dialkylaminoalkyl, $R_5$ is alkyl, alkenyl, aryl or an aromatic or non-aromatic heterocyclic radical containing 5 to 6 chain members, $R_6$ is H, alkyl, carboxyalkyl, aminoalkyl, hydroxyalkyl, aryl, alan-3-yl, R' is —$OR'_4$ or —$SR'_6$ in which $R'_4$ and $R'_6$ can respectively have the same meanings as $R_4$ and $R_6$, except for the meaning hydrogen, polyoxyethylene, hydroxyalkyl, alan-3-yl and aryl, and R" is hydrogen or alkyl.

By way of particularly preferred UV-filtering compounds used according to the invention, there may be mentioned benzylidene-camphor, 4-[(2-oxo-3-bornylidene)methyl]-phenyl-trimethylammonium methylsulfate, p-methylbenzylidene-camphor, N-(2-ethylhexyl)-3-benzylidene-10-camphosulfonamide, 3-(2-oxo-3-bornylidene-methyl)-benzenesulfonic acid, 2-methyl-5-(2-oxo-3-bornylidene-methyl)benzene-sulfonic acid, 3-benzylidene-2-oxo-10-bornanesulfonic acid, terephthalidene-3,3'-dicampho-10,10'-disulfonic acid, terephthalidene-3,3'-dicampho-10-sulfonic acid, 4-(ethyl 2'-carboxyethyl-acrylate)-benzylidene-camphor, 4'-butoxy-3'-methoxy-3-benzylidene-bornanone, and their salts.

The furocoumarins are chosen more especially from among 8-methoxy-psoralene (8 MOP), 5-methoxy-psoralene (5 MOP), 4,5,8-trimethyl-psoralene, 3-carbethoxy-psoralene, angelicine, 4',5'-dimethyl-angelicine, the pyrido(3-4-h)psoralenes and the pyrido(3-4-c)psoralenes.

Within the scope of the invention, the furocoumarins are administered in conventional forms, either by oral administration or in a topical form.

These forms are known per se in the prior art. As regards such treatments and methods of administration, reference may be made to the articles in the literature and especially Henry H. ROENIGK and Jones S. MARTIN in ARCH. DERMATOL., Vol. 113, December 1977, pages 1667 to 1670, H. HONIGSMANN et al. in British Journal of Dermatology (1979), Vol. 101, pages 369 to 377 and K. WOLFF et al. in British Journal of Dermatology (1977) 96, pages 1 to 10.

The furocoumarins can in particular be taken in the form of pills, tablets, etc. The dose generally taken is of the order of 0.1 to 1 mg/kg and is adapted to the skin sensitivity of each patient.

The benzylidene-camphor or its UV-filtering derivatives defined above are applied in the form of topical compositions and in particular in the form of an oil, emulsion, lotion or gel and can be packaged as aerosols. These compositions contain from 1 to 10% of benzylidene-camphor or of its derivatives and in particular from 2 to 6%.

The compositions based on benzylidene-camphor used in the combination according to the invention can contain various adjuvants usually employed in compositions intended for topical applications in pharmacy, and chosen from among thickeners, softeners, humectants, superfatting agents, emollients, wetting agents, surfactants, preservatives, anti-foaming agents, oils, waxes, colorants and pigments serving to color the composition itself or the skin, or any other ingredient usually employed as an adjuvant in this type of composition.

As the solvent for dissolving the benzylidene-camphor or its derivatives there may be used water, an oil, a wax, a monoalcohol, a polyol or a mixture of these. The monoalcohols or polyols particularly preferred are ethanol, isopropanol, ethylene glycol or glycerol.

A preferred embodiment of the invention consists of using the benzylidene-camphor or its derivatives in the form of an emulsion (cream, milk or unguent) containing - in addition to the benzylidene-camphor derivatives - fatty alcohols, ethoxylated fatty alcohols, fatty acid esters or fatty acid triglycerides, fatty acids, lanoline or waxes, in the presence of water.

Another embodiment consists of lotions such as oily-alcoholic lotions based on lower alcohols such as ethanol or a glycol such as propylene glycol and/or polyols such as glycerol, and oils, or aqueous-alcohol lotions. The composition containing the benzylidene-camphor or one of its derivatives can also be employed in the form of an oily-alcoholic, aqueous or aqueous-alcoholic gel.

The photochemotherapy treatment according to the invention essentially consists of causing the patient to take a furocoumarin in doses of the order of 0.6 mg/kg in the form of tablets or pills 2 to 3 hours before he is exposed to UV-A radiation.

A composition containing the benzylidene-camphor or one of its ultraviolet-filtering derivatives is applied in a topical form 10 minutes to 2 hours before exposure to the UV-A radiation. Thereafter, the patient is irradiated in a cabin equipped with a UV-A lamp, the amount of irradiation being 8 to 15 joules/cm$^2$ of skin.

The treatment is carried out two to four times a week and lasts four to twelve weeks. During the treatment, the irradiation dose is increased regularly by about 10% every week. Applicants have thus found that it was possible to treat the skin diseases by photochemotherapy without erythemas or premature ageing of healthy skin.

The invention further relates to the use of benzylidene-camphor or its ultraviolet-filtering derivatives in photochemotherapy treatment.

The examples which follow are intended to illustrate the invention without however being limiting in character.

EXAMPLE 1

A patient suffering from psoriasis patches is caused to take 40 mg of 5-methoxy-psoralene in the form of pills. After an interval of 30 minutes, he is caused to take a second pill containing about 15 mg of 8-methoxypsoralene. After an interval of 2 hours, an unguent having the following composition is applied to the skin:

| | |
|---|---|
| Triethanolamine salt of terephthalylidene-3,3'-dicampho-10-sulfonic acid | 4.0 g |
| Stearyl alcohol | 3.0 g |
| Lanoline | 5.0 g |
| Vaseline | 15.0 g |
| Distilled water to make up to | 100.0 g |

30 minutes later, the patient is exposed to ultraviolet A radiation at a dose of 8 joules/cm$^2$ of skin.

This treatment is continued for 10 weeks at the rate of two to three treatments per week, the irradiation finally being with a dose of about 15 joules/cm$^2$.

The Applicants found that the patient was cured without accelerated ageing or major erythema of the healthy skin.

EXAMPLE 2

The same treatment as that indicated in Example 1 is carried out, but instead of using the unguent described an emulsion having the following composition is applied:

| | |
|---|---|
| Triethanolamine salt of terephthalylidene-3,3'-dicampho-10,10'-disulfonic acid | 3.0 g |
| Benzylidene-camphor | 1.0 g |
| Cetyl alcohol | 3.0 g |
| Stearyl alcohol | 3.4 g |
| Cetyl alcohol oxyethyleneated with 20 moles of ethylene oxide | 0.6 g |
| Stearyl alcohol oxyethyleneated with 20 moles of ethylene oxide | 1.5 g |
| Glycerol monostearate | 2.0 g |
| Vaseline oil | 15.0 g |
| Glycerol | 10.0 g |
| Distilled water to make up to | 100.0 g |

The same result as in Example 1 is obtained.

EXAMPLE 3

The procedure described in Example 1 is followed, but instead of the unguent a composition in the form of a gel is used and is applied to the skin. This gel has the following composition:

| | |
|---|---|
| 4'-butoxy-3'-methoxy-3-benzylidene-camphor | 1.5 g |
| 4-[(2-oxo-3-bornylidene)-methyl]-phenyl-trimethylammonium methyl-sulfate | 2.0 g |
| Hydroxypropylcellulose sold by Ste HERCULES under the name of "KLUCEL HF" | 2.0 g |
| Water/ethanol (20/80) to make up to | 100.0 g |

The same results as above are observed.

We claim:

1. A combination for the photochemotherapy treatment of psoriasis, chronic dermatoses, herpes, vitiligo and alopecia, comprising:
   a first composition containing a therapeutically effective amount of at least one furocoumarin which is activated by UV-A radiation, wherein said effective amount of said furocoumarin is effective for the treatment of diseases selected from the group consisting of psoriasis, chronic dermatoses, herpes, vitiligo and alopecia and said activated furocoumarin and said UV-A radiation cause phototoxic side effects; and
   a second composition containing an effective amount of a benzylidene-camphor or a derivative thereof, wherein said effective amount of said benzylidene-camphor reduces said phototoxic side effects,
   wherein said second composition is applied topically to an area of skin of a patient prior to exposure of said area to said UV-A radiation but after said first composition is administered to the patient.

2. The preparation of claim 1, wherein said benzylidene-camphor derivative is selected from the group consisting of
   (i) 3-p-oxybenzylidene-boran-2-ones of the formula:

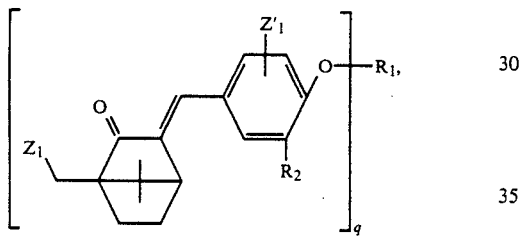

wherein
   $Z_1$ and $Z'_1$ are respectively a hydrogen atom or an $SO_3H$ radical or a salt of the sulfonic acid with an inorganic or organic base and at least one of $Z_1$ or $Z'_1$ is a hydrogen atom;
   $R_1$ is a hydrogen atom, a branched alkyl radical containing 2 to 18 carbon atoms, an alkenyl radical containing 3 to 18 carbon atoms or a radical selected from the group consisting of

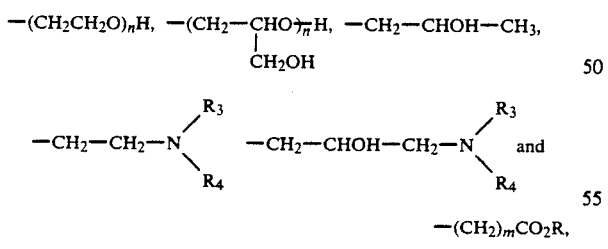

in which R is hydrogen, an alkyl radical containing 1 to 8 carbon atoms, $-(CH_2)_3-SO_3H$ or a salt of this acid with an organic or inorganic base, a divalent radical $-(CH_2)_m-$ or $-CH_2-CHOH-CH_2$, m has a value of 1 to 10, n has a value of 1 to 6 and $R_3$ and $R_4$ each represent a hydrogen atom or a branched or hydroxylated alkyl radical or together form a heterocyclic aminoaliphatic radical with the nitrogen atom;
   $R_2$ is a hydrogen atom, an alkoxy radical containing 1 to 4 carbon atoms or a divalent radical $-O-$ bonded to the $R_1$ radical if the latter is also divalent, q is 1 or 2, with the proviso that if q has a value of 2, $R_1$ is a divalent radical and that if $R_1$ is hydrogen, $R_2$ is also hydrogen and moreover, if $R_3$ is alkoxy, $R_1$ can be methyl;

(ii) benzylidene-camphor derivatives which have the formula:

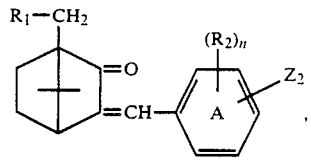

wherein $R_1$ is a hydrogen atom or a $-SO_3M^+$ radical in which M is a hydrogen atom, an alkali metal or an $N^+(R_3)_4$ group, $R_3$ is a hydrogen atom or $C_1-C_4$ alkyl or hydroxyalkyl radical, $R_2$ is a $C_1-C_4$ alkyl radical which may be linear or branched, or a $C_1-C_4$ alkoxy radical, n is an integer ranging from 0 to 4, and, if $n \geq 2$, then the radicals $R_2$ can be identical or different, and Z is a

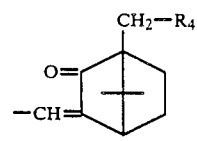

group in which $R_4$ has the same meanings as $R_1$ and can be identical with or different from $R_1$, or Z is a

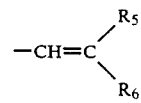

group in which $R_5$ is a hydrogen atom, a $C_1-C_4$-alkyl radical, an aryl radical, which is unsubstituted or substituted by halogen atoms or by $C_1-C_4$-alkyl or alkoxy groups, a $-CN$, $-COOR_7$ or a

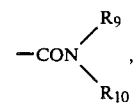

group, and $R_6$ is a $-COOR_8$ or

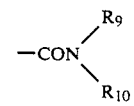

group, where $R_7$ and $R_8$, which may be identical or different, are alkyl, alkenyl, cycloalkyl or aralkyl radicals containing at most 20 carbon atoms and substituted by hydroxyl, alkoxy, amine or quaternary ammonium groups and $R_9$ and $R_{10}$, which may be identical or different, are a hydrogen atom or alkyl, alkenyl, cycloalkyl or aralkyl radicals containing at about 20 carbon atoms substituted by hydroxyl, alkoxy, amine or quaternary ammonium groups, or if $R_5$ is a hydrogen atom or a substituted aryl or alkyl radical, $R_6$ can be a —COO—$M^+$ radical, M defined as above, and the two radicals, the methylidene-camphor and Z radicals, are fixed to the aromatic ring, A, either in the para-position or in the meta-position relative to one another;

(iii) sulfonamides which are derived from 3-benzylidene-camphor and have the formula:

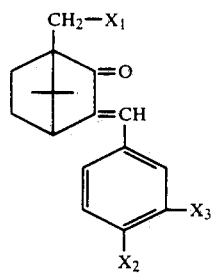

in which $X_1$ is a hydrogen atom or the radical Y, $X_2$ is a hydrogen or halogen atom, a $C_1$–$C_4$-alkyl or alkoxy radical or a radical Y or Z, $X_3$ is a hydrogen or halogen atom, a $C_1$–$C_4$-alkyl or alkoxy radical or a Y or Z radical, Y denotes the

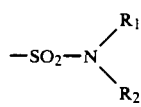

group in which $R_1$ is a hydrogen atom or a $C_1$–$C_4$-alkyl or hydroxyalkyl radical, $R_2$ is a hydrogen atom or a linear or branched alkyl or alkenyl radical or a cycloalkyl, aryl or aralkyl radical, wherein said $C_1$–$C_{20}$ radicals are unsubstituted or are substituted by one or more hydroxyl, alkoxy or dialkylamino groups, but $R_1$ and $R_2$ cannot simultaneously be a hydrogen atom, and Z is selected from the group consisting of $Z_1$, $Z_2$ and $Z_3$ is

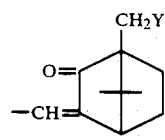

where Y has the meaning given above, or $Z_2$ is

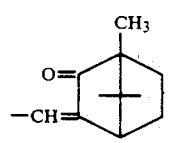

or $Z_3$ is

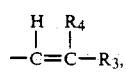

where $R_3$ is a hydrogen atom or —CN or a $COR_5$ radical, $R_4$ is a —$COR_6$ radical and $R_5$ and $R_6$, which may be identical or different, are $C_1$–$C_{20}$-alkoxy or alkylamino groups, with the proviso that one of $X_1$, $X_2$ and $X_3$ is different from the two others with the proviso that:

(a) if $X_1$ is a hydrogen atom, $X_2$ and $X_3$ are different from one another, are not the same as $Z_2$ and $Z_3$, and one of the two obligatorily having the meaning of Y or $Z_1$, and (b) if $X_1$ is Y, then $X_2$ and $X_3$ are different from Y and cannot simultaneously be the same as $Z_1$ or $Z_2$ or $Z_3$;

(iv) benzylidene-camphor derivatives which contain the camphor in the para-position relative to the bornylidene radical and have the formula:

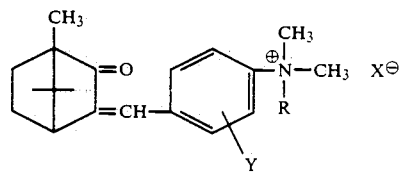

wherein R is a hydrogen atom or an alkyl group containing 1 to 12 carbon atoms, Y is a halogenatom, a methyl group or a hydrogen atom and X is a halide, an arylsulfonate, an alkylsulfonate, a campho-sulfonate or an alkyl-sulfate;

(v) benzylidene-camphor derivatives which are sulfonated at the methyl radical in the 10-position of the camphor or in the 3'- or 4'-position of the benzene ring, which have the formula:

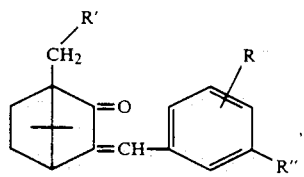

wherein R is a hydrogen atom, a halogen atom or an alkyl radical containing 1 to 4 carbon atoms and R' and R" are each a hydrogen atom, a —$SO_3M$ radical in which M is hydrogen, an organic ammonium group or a metal, in which at least one of the radicals R' and R" are other than hydrogen;

(vi) benzylidene-camphor derivatives which have the formula:

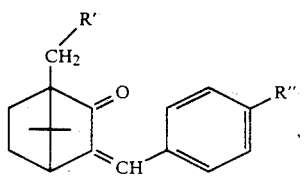

wherein R' is a hydrogen atom of an —$SO_3M$ radical and R" is $SO_3M$, in which M is hydrogen, an organic ammonium group or a metal; and (vii) p-methylenebenzylidene-camphor and p-methylbenzylidene-camphor derivatives, substituted at the p-methyl group, which have the formula:

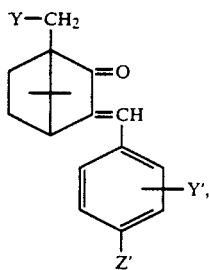

wherein Y and Y' are hydrogen or $SO_3H$ and the corresponding salts with organic or inorganic bases, at least one of the radicals Y and Y' is hydrogen, Z' is a group selected from $—CH_2R$, $—CHR'R'$, $—CHO$, and $—COOR''$, in which $R = —OR_4$, $—OCOR_5$ $—SR_6$, $—CN$ or $—COOR''$, $R_4$ is hydrogen, alkyl, polyoxyethylene, substituted or unsubstituted aryl, methyl or dialkylaminoalkyl, $R_5$ is alkyl, alkenyl, aryl or an aromatic or non-aromatic heterocyclic radical containing 5 to 6 chain members, $R_6$ is hydrogen, alkyl, carboxyalkyl, aminoalkyl, hydroxyalkyl, aryl, alan-3-yl, R' is $—OR'_4$ or $—SR'_6$ in which $R'_4$ and $R'_6$ can respectively be the same as $R_4$ and $R_6$, except that they are not hydrogen, polyoxyethylene, hydroxyalkyl, alan-3-yl and aryl, and R' is hydrogen or alkyl.

3. The combination of claim 2, wherein the benzylidene-camphor derivative is selected from the group consisting of 4'-butoxy-3'-methoxy-3-benzylidene-bornanone, terephthalylidene-3,3'-dicampho-10-sulfonic acid and terephthalylidene-3,3'-dicampho-10,10'-disulfonic acid as well as their salts, 4-(ethyl 2'-carboxyethyl)-acrylate-benzylidene-camphor, benzylidene-camphor, p-methylbenzylidene-camphor, 4[(2-oxo-3-bornylidene)-methyl]-phenyl-trimethylammonium methylsulfate, N-(2-ethyl-hexyl)-3-benzylidene-10-camphosulfonamide, 3-(2-oxo-3-bornylidene-methyl)-benzene-sulfonic acid, 2-methyl-5-(2-oxo-3-bornylidene-methyl)-benzene-sulfonic acid and 3-benzylidene-2-oxo-10-bornane-sulfonic acid as well as their salts.

4. The combination of claim 1, wherein the furocoumarin is selected from the group consisting of 8-methoxypsoralene, 5-meth-oxypsoralene, 4,5,8-trimethyl-psoralene, 3-carbethoxy-psoralene, angelicin, 4'5'-dimethyl-angelicin, the pyrido (3-4-n) psoralenes and the pyrido (3-4-c) psoralenes.

5. The combination of claim 1, wherein the furocoumarin is in a form in which it can be taken orally and the benzylidene-camphor or one of its derivatives is in a form which can be applied topically.

6. The combination of claim 1, wherein the furocoumarin is in the form of tablets or pills and the composition containing the benzylidene-camphor or one of its UV-filtering derivatives is in the form of an oil, lotion, emulsion or gel, wherein said emulsion is a cream, unguent or milk.

7. The combination of claim 1, wherein the composition containing the benzylidene-camphor or one of its derivatives contains pharmaceutical adjuvants selected from the group consisting of thickeners, superfatting agents, emollients, wetting agents, surfactants, preservatives, anti-foaming agents, oils, waxes, colorants and pigments.

8. The combination of claim 1, wherein the composition containing the benzylidene-camphor or one of its derivatives constitutes an emulsion and additionally comprising fatty alcohols, ethoxylated fatty alcohols, fatty acid esters or fatty acid triglycerides, fatty acids, lanoline, oils and waxes, in the presence of water.

9. The combination of claim 1, wherein the composition containing the benzylidene-camphor derivative constitutes an oily-alcoholic or aqueous-alcoholic lotion.

10. The combination of claim 1, wherein the composition containing the benzylidene-camphor derivative constitutes an oily-alcoholic, aqueous or aqueous-alcoholic gel.

11. A method of treating by photochemotherapy psoriasis, chronic dermatoses, herpes, vitiligo and alopecia with reduced phototoxic side effects which comprises:
administering a therapeutic amount of at least one furocoumarin to said patient;
applying an amount of a benzylidene-camphor to the areas of the skin of said patient which are to be exposed to UV-A radiation effective to reduce the phototoxic effect caused by said furocoumarin UV-A radiation therapy, said benzylidene-camphor being in the form of a composition suitable for topical application; and
exposing said patient to UV-A irradiation.

* * * * *